(12) United States Patent
Schmitt et al.

(10) Patent No.: US 8,172,927 B2
(45) Date of Patent: May 8, 2012

(54) APPARATUS AND METHOD FOR FILTERING SECTIONING WASTES OF A MICROTOME THAT ARE PRESENT IN AN AIR STREAM

(75) Inventors: Christoph Schmitt, Schriesheim (DE); Roland Walter, Neulussheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 13/221,697

(22) Filed: Aug. 30, 2011

(65) Prior Publication Data

US 2011/0308334 A1    Dec. 22, 2011

Related U.S. Application Data

(63) Continuation of application No. 12/349,411, filed on Jan. 6, 2009, now Pat. No. 8,048,206.

(30) Foreign Application Priority Data

Feb. 8, 2008   (DE) .......................... 10 2008 000 262

(51) Int. Cl.
   *B01D 50/00* (2006.01)
(52) U.S. Cl. ................ 95/278; 95/287; 55/283; 55/301; 55/482; 55/486
(58) Field of Classification Search .................... 95/278, 95/287, 283, 301, 482, 486
   See application file for complete search history.

(56) References Cited

U.S. PATENT DOCUMENTS

| | | | |
|---|---|---|---|
| 3,191,476 A | 6/1965 | McCormick | |
| 3,723,226 A | 3/1973 | Pfohler | |
| 4,024,779 A | 5/1977 | Taugner et al. | |
| 5,255,585 A | 10/1993 | Gordon | |
| 5,740,708 A | 4/1998 | Tabone | |
| 5,746,855 A | 5/1998 | Bolles | |
| 5,974,811 A | 11/1999 | Heid et al. | |
| 2005/0115373 A1 | 6/2005 | Kunkel | |
| 2009/0181422 A1 | 7/2009 | Schmitt et al. | |
| 2009/0181457 A1 | 7/2009 | Schmitt et al. | |

FOREIGN PATENT DOCUMENTS

| | | |
|---|---|---|
| DE | 1 748 387 | 7/1957 |
| DE | 20 28 898 | 12/1971 |
| DE | 25 06 255 | 9/1976 |

(Continued)

OTHER PUBLICATIONS

Office Action dated Apr. 15, 2011 in related published U.S. Appl. No. 12/349,411, filed Jan. 6, 2009.

(Continued)

*Primary Examiner* — Robert A Hopkins
(74) *Attorney, Agent, or Firm* — Alexander R. Schlee; Schlee IP International, P.C.

(57) ABSTRACT

An apparatus and a method for filtering sectioning wastes of a microtome that are present in an air stream are described. The apparatus has an aspiration device with which sectioning waste can be aspirated from a blade region of the microtome with an air stream. A main filter and a prefilter are provided. A valve is provided for opening and closing an opening so that the air stream so that if desired an air stream can be directed through a filter insert in the prefilter for emptying the prefilter into the main filter. According to the method, an air stream that is used for aspirating sectioning waste from a blade region of the microtome is shut off immediately before emptying the prefilter.

13 Claims, 7 Drawing Sheets

FOREIGN PATENT DOCUMENTS

| | | |
|---|---|---|
| DE | 198 03 966 | 9/1998 |
| DE | 102 42 275 | 4/2004 |
| DE | 103 52 578 | 3/2005 |
| EP | 1 094 310 | 4/1999 |
| EP | 0 725 712 | 5/1999 |
| GB | 2 324 857 | 11/1998 |
| JP | 09101242 | 4/1997 |
| JP | 2002031586 | 1/2002 |
| JP | 2006052963 | 2/2006 |
| JP | 2006220559 | 8/2006 |
| WO | 93 05936 | 4/1993 |
| WO | 94/28390 | 12/1994 |

OTHER PUBLICATIONS

Notice of Allowance dated Aug. 9, 2011 in related published U.S. Appl. No. 12/349,411, filed Jan. 6, 2011.

Combined Search Examination Report dated Mar. 13, 2009 for GB application No. GB0820824.1.

APPARATUS AND METHOD FOR FILTERING SECTIONING WASTES OF A MICROTOME THAT ARE PRESENT IN AN AIR STREAM

CROSS-REFERENCE TO RELATED APPLICATION

This application is a continuation application of the U.S. non-provisional patent application Ser. No. 12/349,411 that was filed on Jan. 6, 2009,now U.S. Pat. No. 8,048206, published under the US publication number US 2009-0199716 A1 and claims the priority of the German patent application 102008000262.3 having a filing date of Feb. 8, 2008 and published under the German publication number DE 102008000262 A1. The entire content of the documents US 2009-0199716 A1 and DE 102008000262 A1 is herewith incorporated by reference.

BACKGROUND OF THE INVENTION

The present invention relates to an apparatus and a method for filtering sectioning wastes of a microtome that are present in an air stream. The apparatus encompasses an aspiration device. With the aspiration device, sectioning waste can be aspirated from the blade region of the microtome with an air stream. The aspiration device comprises a main filter in which the sectioning wastes can be filtered from the air. The present invention further relates to a microtome.

Microtomes are known from the existing art, for example from DE 103 52 578 B3, and are used predominantly for the production of thin paraffin sections in the field of biology, medicine, and industrial research. The histological sample, tissue sample, or preparation to be investigated is usually, in a preceding preparation process, embedded in an embedding medium, for example in paraffin, thereby forming a block. The cross section of the block is usually rectangular, but can also be round and in particular of circular configuration. The block is usually mounted on a part of a cassette, in which the tissue sample is located in the preceding preparation process. With this part of the cassette, the block is clamped into a specimen holding device of the microtome. For sectioning, a drive device is provided that guides the sample or block located in the specimen holding device, by means of a relative motion, over a knife arranged on the microtome. The knife is generally horizontally displaceable in a knife holding device, and can be clamped in at an adjustable angle in defined fashion.

For production of an optimum section surface of a block, the microtome can have a trimming function. For that purpose, the knife holding device can be directed manually via a trimming lever toward the vertically movable specimen holding apparatus for initial sectioning operations, in steps that are larger as compared with the actual sectioning thickness. An unusable sectioning waste is produced in this operation, and collects e.g. in a section collection pan of the microtome.

In histology in particular, the specimens to be investigated often involve contaminated or bacterially affected biological material that can be mixed with paraffin from the preparation process. Even when the samples are sectioned correctly with the microtome, a fine sectioning waste unavoidably occurs; this falls down from the microtome knife and is deposited onto parts of the microtome located therebeneath, for example its housing parts, and in particular in open gaps and especially in the section collection pan. Provision can therefore be made for the sectioning waste produced at the blade region of the microtome to be aspirated with the aid of an aspiration device. This is used in particular with cryostat microtomes, as disclosed, for example, in EP 0 725 712 B1. The aspiration device disclosed therein encompasses a main filter in which the sectioning wastes can be filtered out of the air. In other words, the sectioning wastes are retained in the main filter and separated from the air transporting the sectioning wastes. If, for example during the trimming operation, an important part of the sample (or the entire sample) is then inadvertently cut off and aspirated by the aspiration device, the possibility exists of retrieving that section by looking for the corresponding section in the main filter. Confusion can arise in this context, however, with sections from other samples and thus, in some circumstances, from other patients; this must be avoided.

SUMMARY OF THE INVENTION

One object underlying the present invention is therefore to make available an apparatus and a method for filtering sectioning wastes of a microtome that are present in an air stream, in which method inadvertently aspirated histological sections can be retrieved without confusion.

The apparatus according to the present invention of the kind cited above achieving the aforesaid object has an aspiration device with which sectioning waste can be aspirated from a blade region of the microtome with an air stream, the aspiration device comprising: a main filter in which the sectioning wastes can be filtered from the air; and a prefilter for prefiltering the sectioning wastes, wherein the prefilter is arranged between the blade region and the main filter; the prefilter comprises a valve having two valve positions, wherein with the valve assuming a first valve position, the air stream flowing through the prefilter being directed into a flow direction provided for the filtering position; and with the valve in a second valve position that differs from the first valve position, the air stream flowing through the prefilter being directed into a flow direction provided for the emptying position; the filter insert or the filter region of the prefilter has at least one of a mesh-shaped, lattice-shaped, and hole-shaped structure that is configured substantially conically and tapers in the direction of the air stream; the valve is arranged at the downstream end of the conical filter insert or filter region of the prefilter; an opening is provided that can be closed off by the valve, wherein the valve closes the opening when assuming the first valve position so that the air stream is directed through the hole-shaped structure of the filter insert or filter region; and the valve opens the opening when assuming the second valve position so that almost the entire air stream is directed through the opening.

The method for filtering sectioning wastes of a microtome that are present in an air stream is performed according to the present invention by means of an apparatus having an aspiration device comprising a blade in a blade region, a main filter and a prefilter, said method comprising the method steps of: aspirating sectioning waste from the blade region of the microtome with an air stream; filtering sectioning wastes by means of the main filter from the air; arranging the prefilter between the blade region and the main filter; prefiltering the sectioning wastes from the air; emptying the filtered contents of the prefilter to the main filter; and shutting off the air stream immediately before emptying the prefilter.

What has been recognized according to the present invention is firstly that as a result of the provision of the prefilter between the main filter and the blade region of the microtome, the sections belonging to one sample or to one sample block can be intermediately filtered or filtered, and temporarily stored in the prefilter. Advantageously, therefore, there exists no risk of confusing sections from different samples filtered in the intermediate filter when, upon clamping of a different block into the microtome, the intermediate filter is also emptied or its filter insert is replaced or exchanged for a different filter. It is thereby possible to ensure that sectioning wastes or sections of one block or one sample are always filtered in the prefilter and correspondingly retrieved if an important sample part was inadvertently sectioned and aspirated. If it should be necessary, the possibility exists of storing the filter insert of the prefilter, along with the sections and sectioning waste filtered therein, together with the remainder of the block or sample for later investigation, for example in forensic medicine.

According to a preferred embodiment, the filtered contents of the prefilter can be emptied to the main filter. This can be implemented in design terms in many ways, and some possibilities for this are discussed in more detail below merely by way of example. The prefilter thus has the function of a temporary reservoir for the sectioning wastes aspirated by the aspiration device, until said reservoir is emptied to the main filter. Because the prefilter can be emptied to the main filter, it is thereby embodied, in particular, in self-cleaning fashion. The prefilter can, however, also be embodied in self-cleaning fashion in another manner, as is usual for example in filter technology.

According to a very particularly preferred embodiment, sectioning wastes are retainable with the prefilter, and the filtered sectioning wastes are conveyable to the main filter only when all the sections of a block that are to be produced with the microtome have been produced. Only the sectioning wastes of one block are thus retained in the prefilter, with the result that confusion-free location or retrieval of an inadvertently aspirated section can be guaranteed, provided the filter was emptied upon clamping of a block into the microtome. In this exemplifying embodiment, the prefilter thus has the function of a temporary reservoir for the sectioning wastes of a single block or a single sample aspirated by the aspiration device, until said filter is emptied to the main filter.

The prefilter emptying operation could be performable manually, or could be capable of manual and/or automatic initiation, as a function of the physical embodiment of the prefilter. Manual execution of the prefilter emptying operation could be accomplished, for example, by actuating an emptying lever, with which the microtome operator actuates an emptying mechanism of the prefilter. The emptying operation could be initiated manually, for example by pressing a button, in which context an emptying mechanism of the prefilter could then be actuated in motorized fashion. Particularly preferably, the prefilter emptying operation can be initiated in automated fashion, namely in particular when a new block is clamped into the microtome. For this purpose, a sensor could be provided on the specimen holding device of the microtome, with which the operation of changing blocks in the microtome is detected and is conveyed to a control device. As soon as a change operation has been detected, the control device could automatically activate the prefilter emptying operation, and authorize the microtome again for the production of sections only when the prefilter emptying operation is entirely completed.

A means for temperature control, with which the prefilter and/or main filter can be cooled or heated, is preferably provided. Cooling of the prefilter is helpful especially during sectioning operation, since the individual histological sections then do not adhere or stick to one another and/or to the filter or filter insert, so that the cleaning operation can thus be performed more easily and more quickly. The means for temperature control could, for example, heat the prefilter or the filter insert of the prefilter in the context of the cleaning or emptying operation, so that the sectioning waste can be cleared as completely as possible out of the prefilter.

According to a preferred embodiment, the prefilter comprises a filter insert or a filter region that has a mesh-, lattice- and/or hole-shaped structure. The mesh-, lattice- and/or hole-shaped structure is dimensioned in such a way that the sectioning wastes usually resulting during the microtome sectioning operation are retainable by the filter insert or filter region, and in particular that the air used to transport the sectioning wastes can pass through. The mesh-, lattice-, and/or hole-shaped structure of the filter insert or filter region is preferably configured and/or dimensioned in such a way that small tissue samples, for example biopsies or punches, are retainable by the filter insert. The mesh-, lattice-, and/or hole-shaped structure could in this context have a lattice spacing and/or holes or orifices that are on the order of 0.05 mm to 0.5 mm, preferably 0.2 mm.

Design configurations with which the filter can be emptied or cleared to the main filter are discussed below. This can be achieved, in particular, with the device for air stream reversal, or with a valve, associated with the prefilter, for switching over the air stream.

The device for air stream reversal will be discussed first; according to this, the prefilter comprises a device for air stream reversal of the filter insert, with which device the filter insert can be transferred from a filtering position, in which sectioning wastes are filterable, to an emptying position, in which the filter insert can be emptied to the main filter. The prefilter is thus in at least two positions or states, namely in a filtering state and in an emptying state. The prefilter or filter insert is transferred between the two positions or states with the device for air stream reversal, or the air stream is reversed by the device for air stream reversal. Provision can be made for shutting off the air stream during the switchover operation.

With the device for air stream reversal the filter insert could thus be rotatable or reversible or pivotable with regard to the air stream direction. In this context, the filter insert and an optionally provided holder for the filter insert are rotatable about a rotation axis arranged substantially perpendicular to the air stream direction, in order to effect the air stream reversal of the filter insert. In other words, the filter insert can be rotated substantially through 180 degrees about the rotation axis arranged perpendicular to the air stream direction, so that after rotation of the filter insert, the air stream acts in the opposite direction and the sectioning wastes caught in the filter insert are emptied to the main filter.

Alternatively thereto, the filter insert can be rotatable or pivotable about a rotation axis arranged substantially parallel to the air stream direction, in order to effect the air stream reversal of the filter insert. The device for air reversal could thus comprise a first and a second connector part, the first connector part being connectable to an upstream or a downstream duct of the aspiration device, and the second connector part being connectable to a downstream or an upstream duct of the aspiration device. When the first connector part is connected to an upstream duct of the aspiration device, the second connector part is connected to a downstream duct of the aspiration device, and vice versa. The filter insert would usefully need to be arranged between the first and the second connector part of the device for air reversal. According to this embodiment, not only does the filter insert need to be rotated or pivoted about the rotation axis arranged substantially parallel to the air stream direction, but a corresponding housing part of the device for air reversal, in which the filter insert is arranged, also needs to be moved.

In order to effect the air stream reversal of the filter insert, the filter insert could also be rotatable or pivotable about a rotation axis arranged substantially parallel to the air stream direction if the device for air reversal comprises a rotary member having at least one receptacle for a filter insert. The rotary member is rotatable into the filtering position in such a way that the filter insert, arranged in a receptacle, is assignable to the upstream duct of the aspiration device. In this context, the part or region of the filter insert serving for filtration is impinged upon by air and sectioning wastes. The rotary member is rotatable into the emptying position in such a way that the filter insert, arranged in the receptacle, is assignable to the downstream duct of the aspiration device. In this position, the back side of the part or region of the filter insert serving for filtration is impinged upon by air so that, as a result, the sectioning wastes present in the part/region serving for filtration are blown or transported toward the main filter. The rotary member could be embodied in rotationally symmetrical fashion and comprise multiple receptacles each for one filter insert, for example two receptacles for filter inserts.

Concretely, the upstream duct of the aspiration device and the downstream duct of the aspiration device could be arranged substantially parallel to one another. The device for air reversal has a substantially U-shaped duct layout, and can be arranged on connector parts, arranged next to one another, of the upstream and downstream ducts of the aspiration device (at the top). The rotation axis of the rotary member is arranged substantially parallel to the upstream and the downstream duct of the aspiration device, or to their longitudinal axis. Further details in this regard are given in the description of the Figures, and reference is therefore made to that part of the Specification. The device for air reversal has a duct layout with which the upstream duct of the aspiration device is connectable to the downstream duct of the aspiration device.

Alternatively thereto, the upstream duct of the aspiration device and the downstream duct of the aspiration device could be arranged at a predefinable angle to one another, for example 90 degrees. In this case the device for air reversal has a duct layout with which the upstream duct of the aspiration device is connectable to the downstream duct of the aspiration device. The rotation axis of the rotary member is preferably arranged substantially in the direction of the angle bisector of the angle between the upstream and the downstream duct of the aspiration device, in the above example at an angle of 45 degrees to the upstream and the downstream duct of the aspiration device. The filter insert can, in this context, be arranged with its effective filter surface preferably substantially perpendicular to the air stream direction, or less preferably at a different angle, in particular at the angle of the angle bisector of the angle between the upstream and the downstream duct of the aspiration device. This alternative can be useful, in particular, when such a construction is necessary because of limited space conditions on the microtome, i.e. for example when an "around-the-corner" duct layout of the aspiration device is necessary.

In other words, according to these exemplifying embodiments, air reversal of the filter insert and thus emptying of the prefilter are effected by the fact that the filter insert is rotated or pivoted relative to the aspiration device. Alternatively thereto, the prefilter can be emptied to the main filter by the fact that the filter insert is arranged in substantially stationary fashion in the aspiration device, but the air flow is redirected.

For redirection of the air stream, according to a preferred embodiment the prefilter comprises a valve having two valve positions. In one valve position, the air stream flowing through the prefilter is directable by the valve into a flow direction provided for the filtering position. In a different valve position, the air stream flowing through the prefilter is directable by the valve into a flow direction provided for the emptying position. A concrete embodiment thereof is discussed below. Assuming corresponding duct layouts for both the downstream and the upstream ducts of the aspiration device, a redirection of the air stream could also be achieved with two or more valves each having two valve positions, the duct layout for this being somewhat more complex.

If only one valve having two valve positions is provided, the filter insert or the filter region of the prefilter having the mesh-, lattice-, and/or hole-shaped structure could be configured substantially conically, preferably tapering in the direction of the air stream. Concretely, the conical shape of the filter insert or of the filter region could be embodied in a conical or truncated pyramidal shape. The valve could be arranged at the downstream end of the conical filter insert or filter region of the prefilter. An opening can be closed off by the valve. In the closed position of the valve, the opening is closed and the air stream is directable through the mesh-, lattice-, and/or hole-shaped structure of the filter insert or filter region, with the result that sectioning wastes are caught by the filter insert or filter region. This is the filtering state of the prefilter. In the opened position of the valve, almost the entire air stream is directable through the opening. In this valve position, the air stream does not pass, or passes in only insignificant fashion, through the mesh-, lattice-, and/or hole-shaped structure of the filter insert or filter region. This is the emptying position of the prefilter.

According to an embodiment, the main filter comprises a comminution unit with which the sectioning wastes in the main filter can be comminuted. The sectioning wastes can thereby be collected in the main filter in space-saving fashion. A fill level sensor could be provided which, when the main filter is full, outputs a signal so that an operator empties the main filter or replaces the filter insert of the main filter, or shuts off the air stream and/or inhibits operation of the microtome.

According to a very particularly preferred embodiment, the apparatus according to the present invention comprises an isolating device as described in one of claims 1 to 18 of DE 10 2008 000 035.3, or is integrated into the isolating device. The histological sections produced by the microtome, which usually form a section strip, can be isolated using the isolating device. The isolating apparatus encompasses a nozzle device with which a histological section positioned on the blade holder can be impinged upon by an air stream. In this context, the direction and intensity of the air stream are adjusted in such a way that a previously produced histological section of a section strip, which section is connected to the histological section positioned on the blade holder, is separable therefrom and removable from the blade holder. With regard to further details of the isolating apparatus, reference is made to DE 10 2008 000 035.3, the entire content of which is incorporated herein. The apparatus for filtering sectioning wastes is preferably associated with the nozzle device of DE 10 2008 000 035.3, or is integrated thereinto. For example, the prefilter could be arranged in the suction conduit of the nozzle device in front of filter device 22 of FIG. 5 of DE 10 2008 000 035.3, filter device 22 corresponding to the main filter for purposes of the present invention.

A microtome according to the present invention for the production of histological sections comprises an apparatus as described above in detail for filtering sectioning wastes that are present in an air stream.

Further, the invention encompasses a method achieving the above mentioned object of the invention. In accordance there-with, according to the method according to the present invention sectioning waste is aspirated with an air stream, using an aspiration device, from the blade region of the microtome. The aspiration device comprises a main filter in which the sectioning wastes are filtered out of the air. The aspiration device comprises a prefilter, arranged between the blade region and the main filter, in which the sectioning wastes are prefiltered. The method according to the present invention serves to filter sectioning wastes of a microtome that are present in an air stream. The method according to the present invention serves in particular for operating the apparatus as described above or for operating a microtome as described above, in order to avoid repetition, reference is therefore made to the foregoing portion of the Specification regarding the apparatus features relevant thereto. The method steps necessary for operating the apparatus described, or the microtome, are apparent in this context to a skilled artisan active in the present sector having knowledge of the disclosure of the foregoing portion of the Specification.

The filtered contents of the prefilter are preferably emptied to the main filter. Very particularly preferably, sectioning wastes are retained by the prefilter; the filtered sectioning wastes are conveyed to the main filter only when all the sections of a block that are to be produced with the microtome have been produced. The prefilter emptying operation could be initiated manually and/or in automated fashion. The emptying operation could, in particular, be initiated in automated fashion when a new block is clamped into the microtome.

Immediately before the prefilter emptying operation, the air stream is shut off. This on the one hand prevents sectioning waste from being transported during the prefilter emptying operation and deposited at unintended locations in the filter apparatus. On the other hand, the prefilter is not already emptied during the switchover operation, which can likewise transport sectioning waste to undesired locations in the filter apparatus.

There are various ways of advantageously embodying and refining the teaching of the present invention. In the following, the invention is described in more detail by discussing preferred exemplifying embodiments of the invention with reference to the drawings. In conjunction with the explanation of the preferred exemplifying embodiments of the invention with reference to the drawings, an explanation is also given of generally preferred embodiments and refinements of the teaching.

DETAILED DESCRIPTION OF THE DRAWINGS

Figure 1:
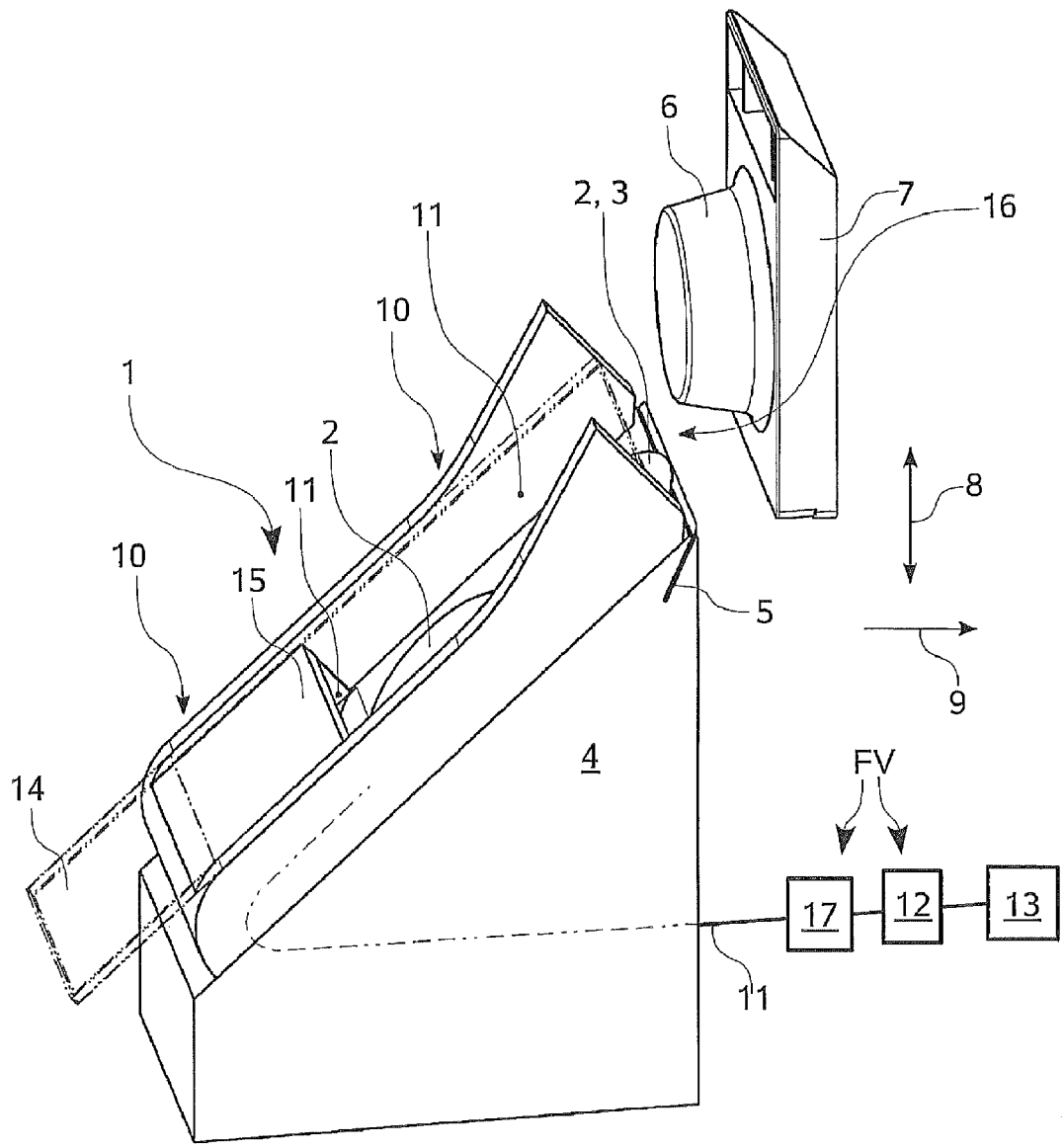
FIG. 1 is a perspective view of an exemplifying embodiment of an apparatus for isolating histological sections, on which apparatus is arranged an apparatus according to the present invention for filtering sectioning wastes of a microtome that are present in an air stream.

In the Figures, identical or similar components are labeled with the same reference characters. FIG. 1 shows an apparatus 1 for isolating histological sections 2 that is known substantially from DE 10 2008 000 035.3. The manner of operation of apparatus 1 is thus also comparable to that of the apparatus disclosed in DE 10 2008 000 035.3. In these exemplifying embodiments, apparatus 1 for isolating histological sections 2 is a constituent of a microtome (not shown in the Figures). Histological sections 2, 3 are produced in such a way that a most recently produced histological section 3 is connected to a previously produced histological section 2 to form a section strip. A section strip can usually comprise multiple histological sections 2, 3. FIG. 1 shows only two histological sections 2, 3, partly concealed by a side wall, connected to form a section strip. Upon production of a histological section 3, a previously produced histological section 2 is moved or shifted along blade holder 4 by the most recently produced histological section 3. In that context, the previously produced histological section 2 moves away from blade 5.

Histological sections 2, 3 were produced from a block 6; block 6 contains a histological sample (not shown in FIG. 1) that is embedded in an embedding medium. It is apparent from the perspective depiction in FIG. 1 that block 6 has substantially a circular cross section and is of truncated conical shape. Histological sections 2, 3 thus likewise have a circular cross section. Block 6 is mounted on a cassette 7. Cassette 7 in turn is clamped in a specimen holder (not shown in the Figures) of a microtome. The specimen holder, together with cassette 7 and block 6, is moved upward and downward in a vertical direction (arrow 8) so that—assuming appropriate specimen advance by a predefinable amount in direction 9 in each case—a histological section 2, 3 is produced as block 6 passes by blade 5 of the microtome. The microtome is accordingly configured in the form of a rotary microtome. The basic manner of operation of a rotary microtome is described, for example, in DE 103 52 578 B3.

Figure 5:
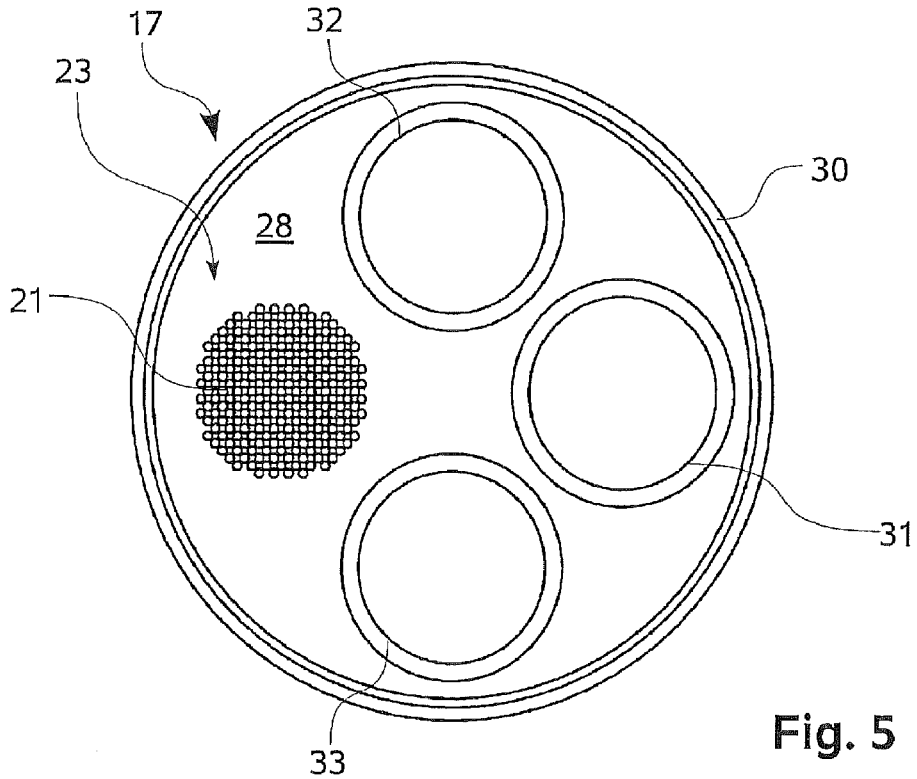
FIG. 5 is a plan view of the rotary member in the position according to FIG. 4.

As already indicated, the manner of operation of apparatus 1 is comparable to that of the apparatus disclosed in DE 10 2008 000 035.3. Apparatus 1 accordingly comprises a suction conduit 11 associated with a nozzle device 10, with which conduit air is aspirated from the region of blade 5 and directed, through the duct (indicated with dashed lines) passing inside blade holder 4, to a main filter 12. In main filter 12, sectioning wastes that are transported in suction conduit 11 with the aid of the air stream are filtered out of the air and retained in the main filter. The negative pressure needed so that the air stream can be drawn through suction conduit 11 is created with the aid of fan 13. The upper side of suction conduit 11 on blade holder 4 is covered with a specimen slide 14 indicated with dashed lines. A histological section 2 is to be applied onto specimen slide 14, for example in a manner comparable to the application apparatus according to DE 10 2008 000 035.3, and in particular as shown and described in FIG. 5 therein. Provided at a distance from blade 5 is constricted region 15 of suction conduit 11 at which the effective flow cross section for the air stream is decreased. The air there accordingly has a higher flow velocity than in a region close to blade 5. An elevated air pressure, which causes the corresponding histological section 2 to be torn off from the section strip, is accordingly present in this constricted region 15. The torn-off histological section 2 is accordingly transported by the air stream in suction conduit 11 to main filter 12.

Apparatus FV according to the present invention for filtering sectioning wastes of a microtome that are present in an air stream comprises an aspiration device having a main filter 12. According to the present invention, a prefilter 17 is arranged between the blade region (indicated with reference character 16) and main filter 12, in which prefilter the sectioning wastes can be prefiltered. Prefilter 17 is arranged before main filter 12 in the direction of the air stream. In the following exemplifying embodiments of prefilter 17 respectively described therein, it can be emptied to main filter 12. In other words, sectioning wastes are retainable in prefilter 17. Very particularly preferably, the filtered sectioning wastes are not conveyed from prefilter 17 to main 12 until all the sections of a block 6 that are to be produced in the microtome have been produced.

Two exemplifying embodiments of different prefilters 17 will be explained below. The first exemplifying embodiment of a prefilter 17 is shown in FIGS. 2 to 9. The second alternative exemplifying embodiment of a prefilter 17 is shown in FIGS. 10 to 13.

Figure 2:
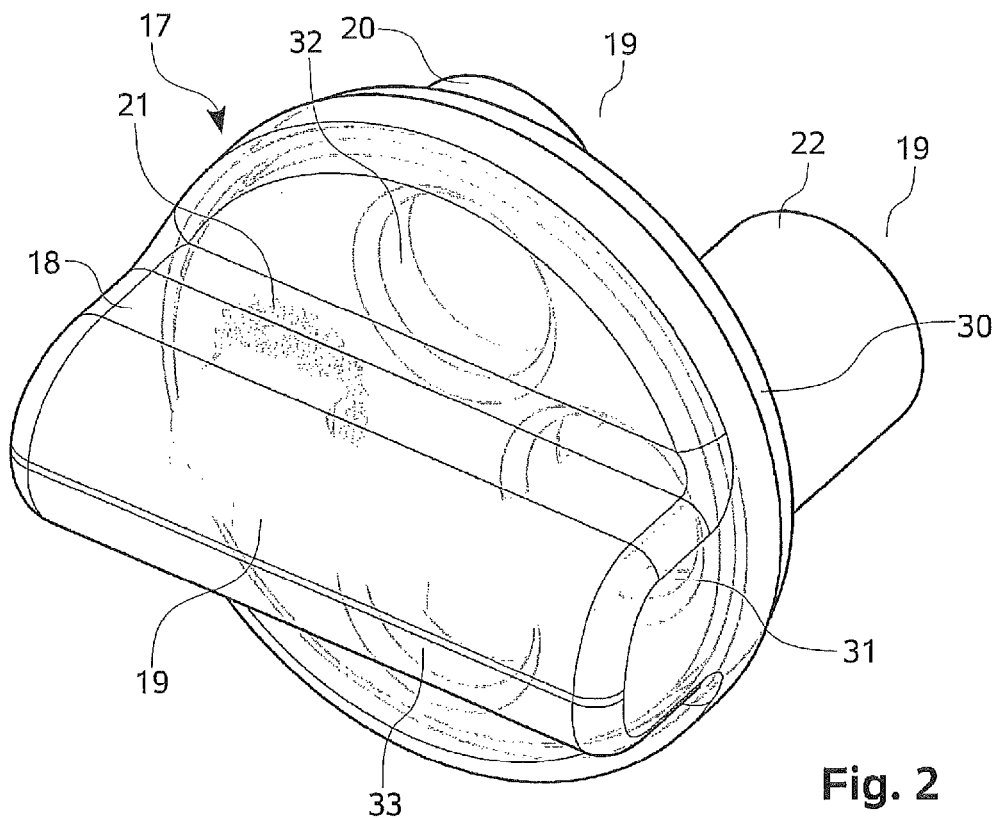
FIG. 2 is a perspective view of an exemplifying embodiment of a prefilter having a device for air reversal of the filter insert.
Figure 3:
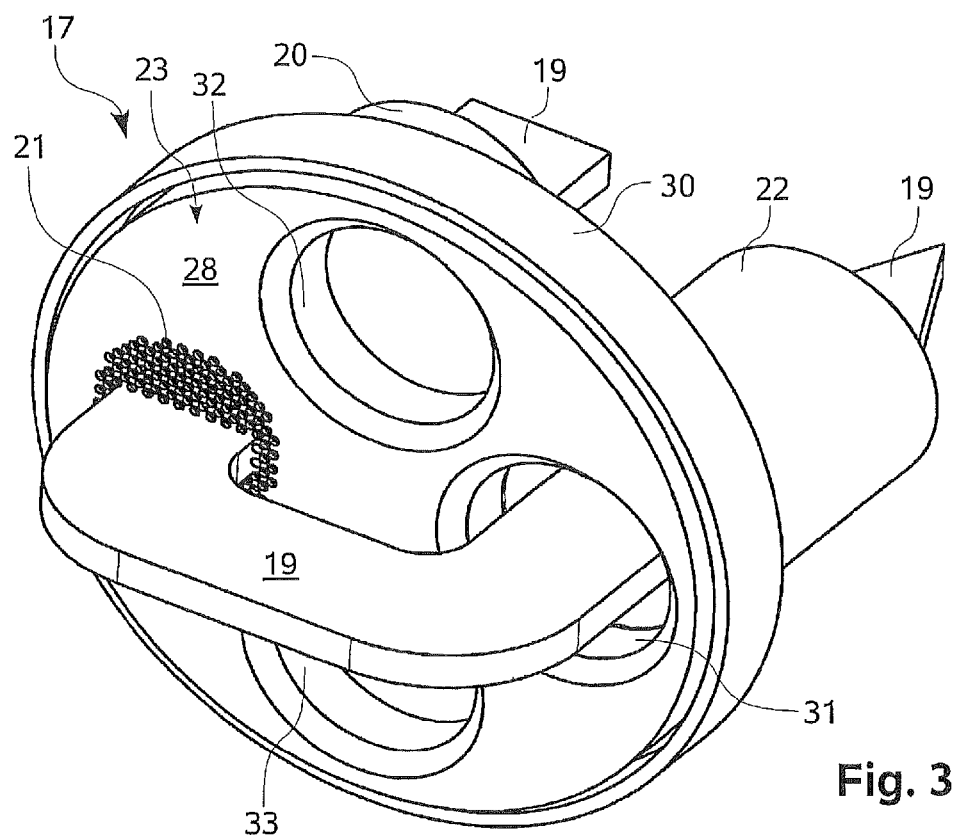
FIG. 3 shows the device for air reversal of FIG. 2, without a covering hood.
Figure 4:
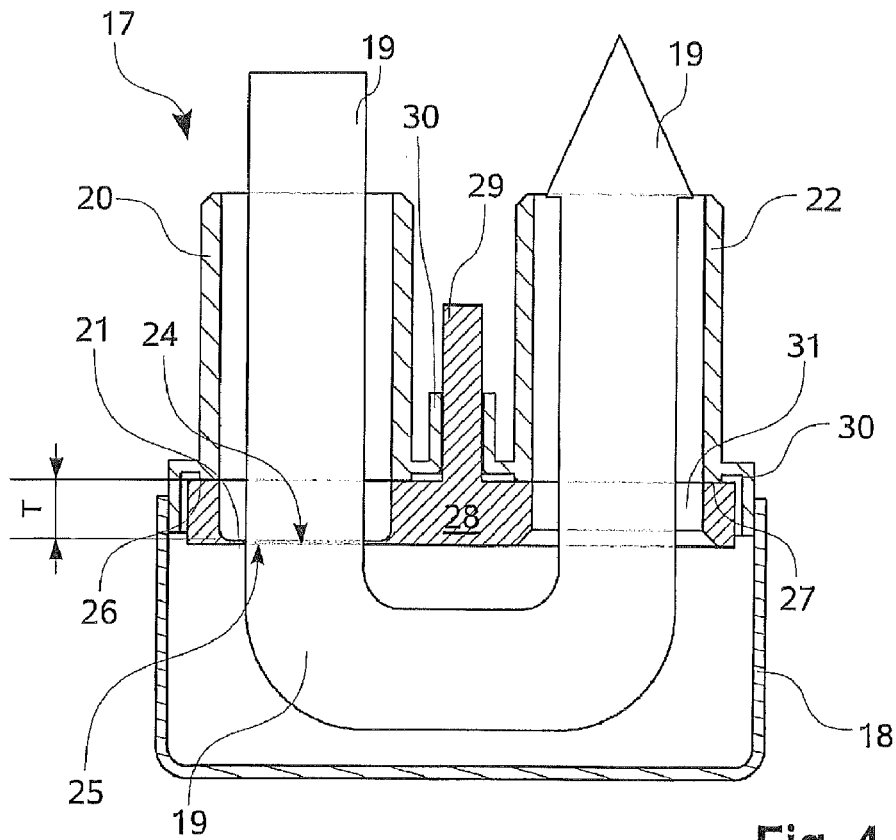
FIG. 4 is a cross-sectional view of the prefilter with the device for air reversal of FIG. 2, in the filtering state.

FIG. 2 is a perspective view showing the first exemplifying embodiment of prefilter 17. Prefilter 17 encompasses a covering hood or filter cover 18 that is shown as partly transparent in FIG. 2. In FIG. 3, prefilter 17 is shown without the removably arranged filter cover 18. In this state, filter insert 21 can be accessed so that it can be, for example, replaced or manually cleaned. Arrow 19 schematically indicates the direction of the air stream flowing through prefilter 17. Air is thus aspirated by fan 13 in such a way that air coming from blade region 16 of the microtome passes through upstream duct 20, through filter insert 21, and is deflected because of filter cover 18 and drawn on through downstream duct 22 to fan 13. Filter insert 21 has a hole-shaped structure, as is evident in particular from FIG. 5, 7, or 9. The diameter of the holes of filter insert 21 is 0.1 mm. Sectioning wastes, in particularly including small tissue samples such as biopsies, are accordingly retained by filter insert 21.

Figure 6:
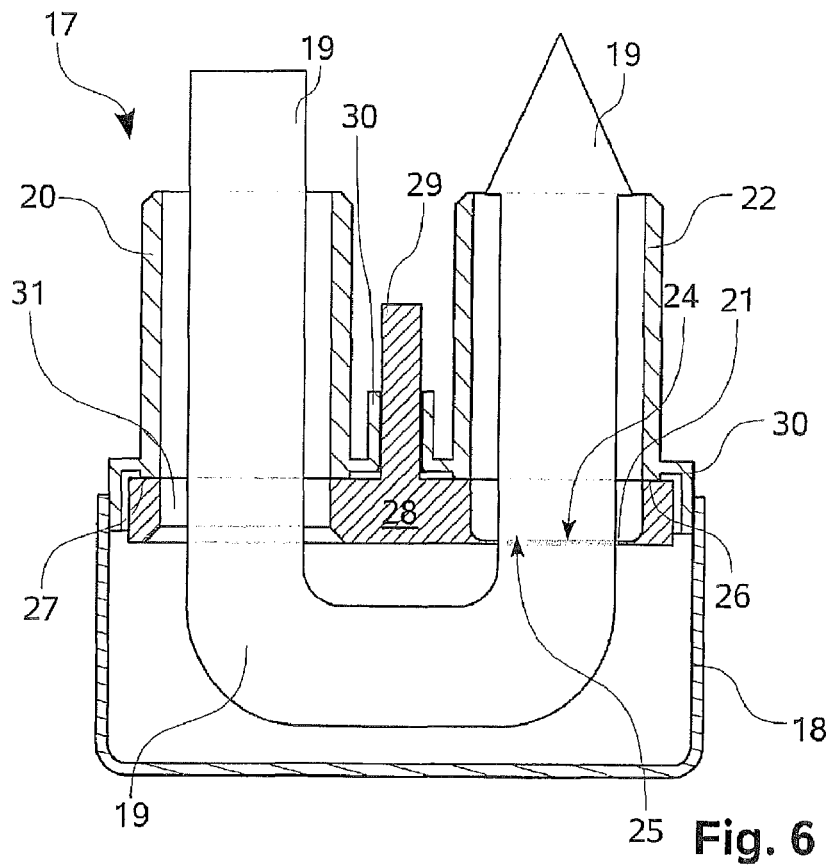
FIG. 6 is a cross-sectional view of the prefilter with the device for air reversal of FIG. 2, in the emptying state.
Figure 7:
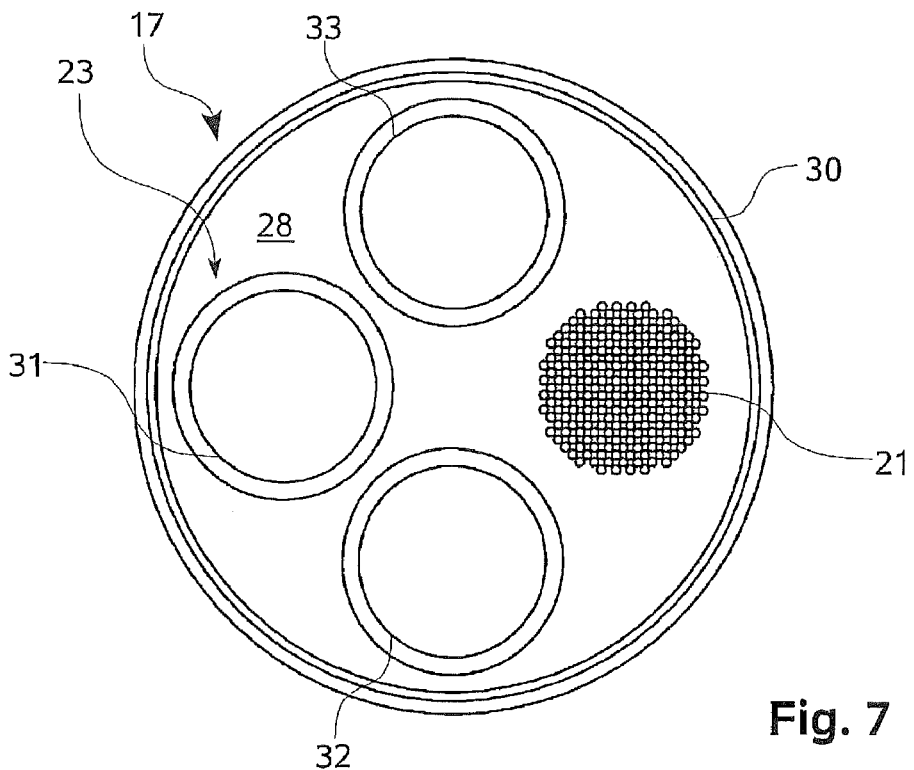
FIG. 7 is a plan view of the rotary member in the position according to FIG. 6.
Figure 8:
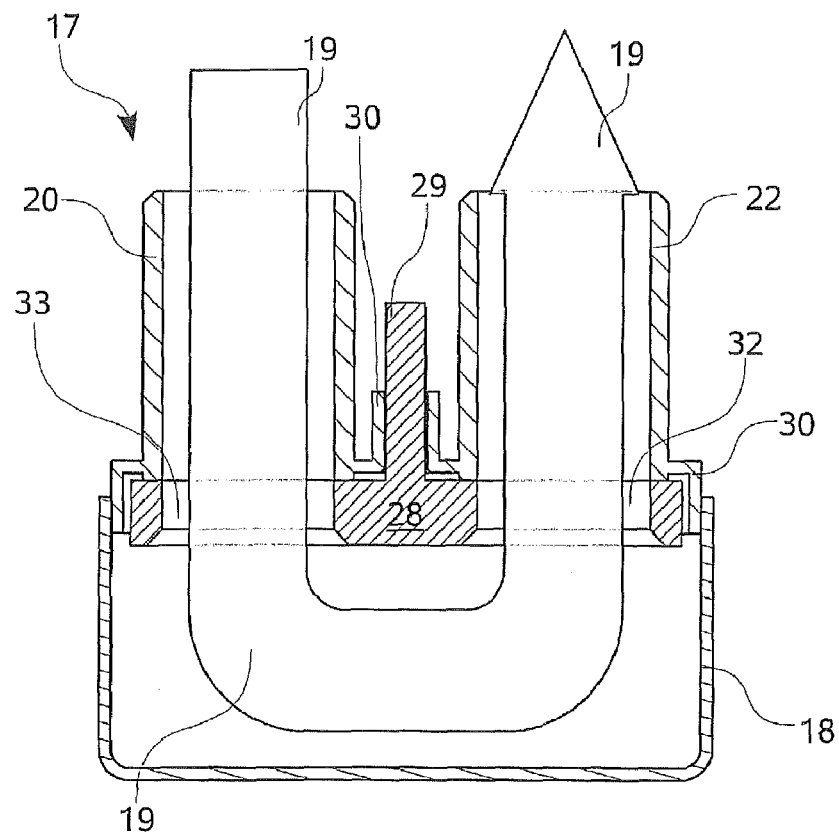
FIG. 8 is a cross-sectional view of the prefilter with the device for air reversal of FIG. 2, in a further state.
Figure 9:
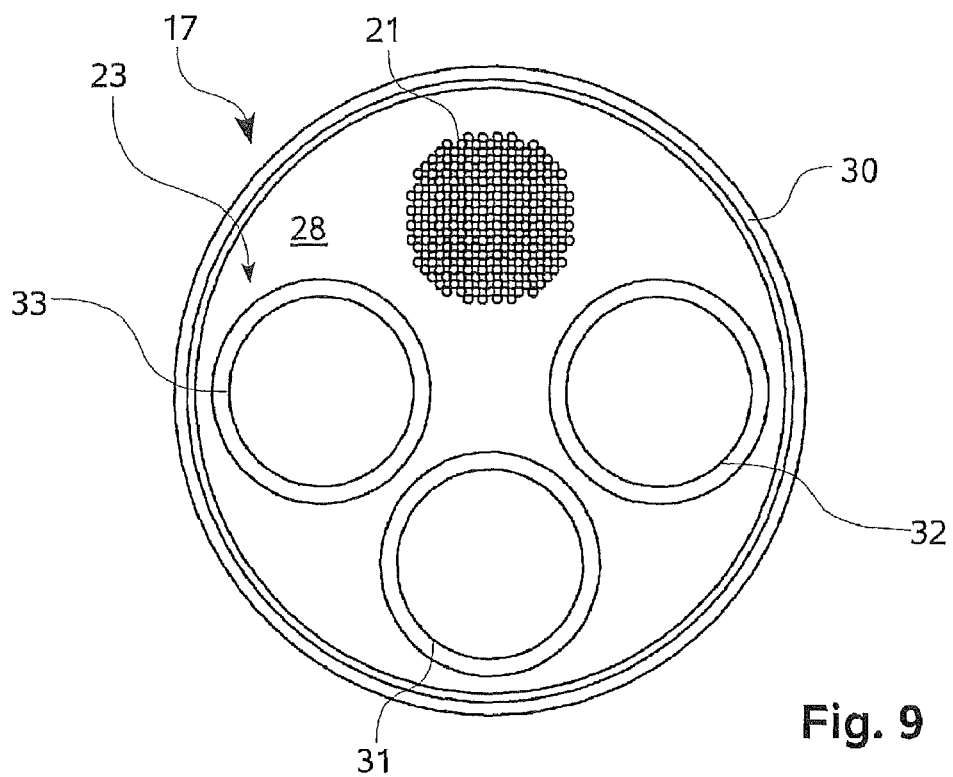
FIG. 9 is a plan view of the rotary member in the position according to FIG. 8.

Prefilter 17 encompasses a device 23 for air reversal of filter insert 21. With device 23 for air reversal, filter insert 21, which is impinged upon by air stream 19, can be transferred into two different positions or states. On the one hand, filter 21 can be transferred by device 23 for air reversal into a filtering position. This is shown in FIGS. 2 to 5. In this position, filter insert 21 is impinged upon by the air stream from side 24 of filter insert 21. Histological sections or sectioning waste (not shown in the Figures) accordingly collect on filter insert 21 on side 24 of filter insert 21. In addition, filter insert 21 can be transferred with device 23 for air reversal into an emptying position. This is shown in FIGS. 6 and 7. In this position, filter insert 21 is impinged upon by the air stream from the other side 25. Because filter insert 21, in the emptying position, is impinged upon by the air stream from the other or opposite side 25, sectioning wastes that have collected on side 24 of filter insert 21 are thereby emptied to main filter 12 and blown away from side 24. Device 23 for air reversal comprises a first connector part 26 that, in the filtering position, is connected to upstream duct 20 (see e.g. FIG. 4). In the emptying position, first connector part 26 is connected to downstream duct 22 (see e.g. FIG. 6). Device 23 for air reversal comprises a second connector part 27 that, in the filtering position, is connected to downstream duct 22 (FIG. 4), and in the emptying position is connected to upstream duct 20 (FIG. 6).

Device 23 for air reversal encompasses, concretely, individual rotary members 28 in which filter insert 21 is received in a receptacle or recess. Depth T of the recess is designed for the average maximum quantity of sectioning wastes from one block 6. Rotary member 28 can be rotated about rotation axis 29 rotatably relative to housing part 30 of prefilter 17, for example from the filtering position shown in FIG. 4 into the emptying position shown in FIG. 6. Also associated with housing part 30 are upstream duct 20 and downstream duct 22. Rotary member 28 further encompasses three holes 31, 32, and 33 that, in principle, could likewise each receive a filter insert, but that in the exemplifying embodiment shown in the Figures do not receive a filter insert. With rotary member 28 in the state shown in FIG. 8, rotary member 28 is in a position in which hole 33 is associated with upstream duct 20, and in which hole 32 is associated with downstream duct 22. In other words, with rotary element 28 in this position, no filter insert is provided in air stream 19. In this operating state of prefilter 17, none of the sectioning waste transported by air stream 19 is retained or filtered in prefilter 17. The sectioning waste is conveyed directly to main filter 12 for filtration.

In the exemplifying embodiment according to FIGS. 2 to 9, upstream duct 20 and downstream duct 22 are arranged parallel to one another. Rotation axis 29 of rotary member 28 is arranged parallel to the longitudinal axes of upstream duct 20 and of downstream duct 22. It is evident in particular from FIGS. 4, 6, and 8 that device 23 for air reversal, and prefilter 17, have a U-shaped duct layout for air stream 19.

Figure 10:
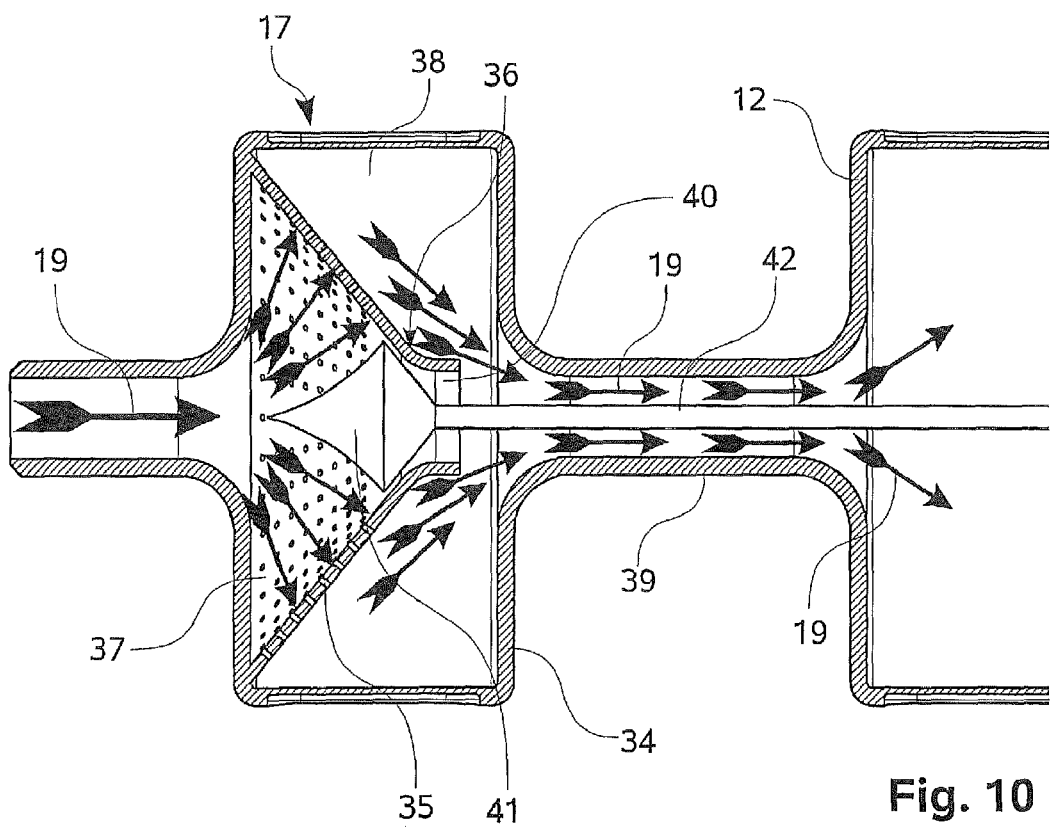
FIG. 10 is a cross-sectional view of a further exemplifying embodiment of an apparatus according to the present invention for filtering sectioning wastes of a microtome that are present in an air stream, the prefilter being in the filtering state.
Figure 11:
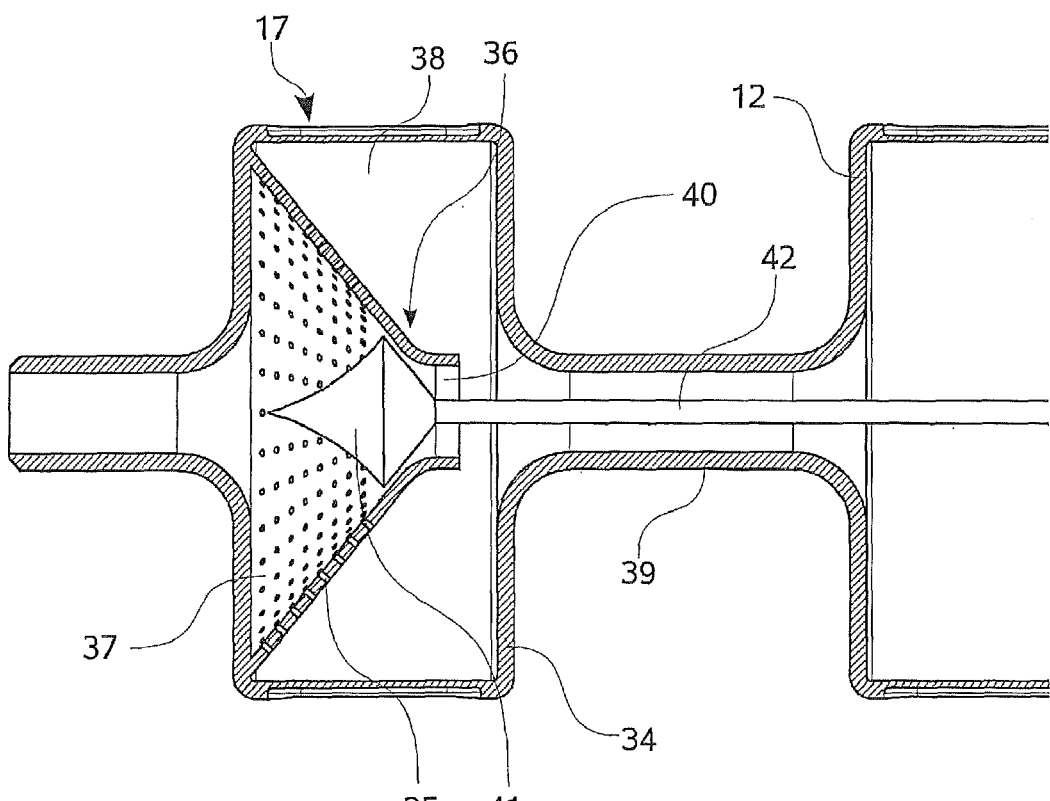
FIG. 11 shows the cross-sectional view of FIG. 10 without the added arrows identifying the air stream direction.

FIGS. 10 to 13 are sectioned views each showing the second alternative exemplifying embodiment of a prefilter 17. In accordance with this exemplifying embodiment, prefilter 17 comprises a substantially rectangular housing part 34. The filter insert or filter region 35 of prefilter 17 is arranged in housing part 34 in stationary fashion with respect to housing part 34. Filter region 35 likewise has a hole-shaped structure. Filter region 35 is embodied conically, tapers in the direction of air stream 19, and has the shape of a truncated cone. Prefilter 17 according to the second exemplifying embodiment comprises a valve 36. Valve 36 has a first valve position that is shown in FIGS. 10 and 11. In this valve position, air flowing into prefilter 17 flows into first chamber 37. Air passes through the hole-shaped structure of filter region 35 and passes into second chamber 38 of prefilter 17, sectioning wastes being retained by the hole-shaped structure of filter region 35. From second chamber 38, air travels through duct 39 into main filter 12. Prefilter 17 is shown in FIG. 10 with valve 36 in the first valve position, the direction of air stream 19 being indicated with arrows. Because air passes through the hole-shaped structure of filter region 35 when valve 36 is in this position, in the operating state shown in FIGS. 10 and 11 prefilter 17 is in the filtering position. FIG. 11 shows prefilter 17 in the same position as in FIG. 10, without the directional arrows. Provided at the end of filter region 35 is opening 40 that can be closed off by closure piece 41 of valve 36. This state is shown in FIGS. 10 and 11. Closure piece 41 can be actuated via rod 42 by a mechanism not shown in the Figures.

Figure 12:
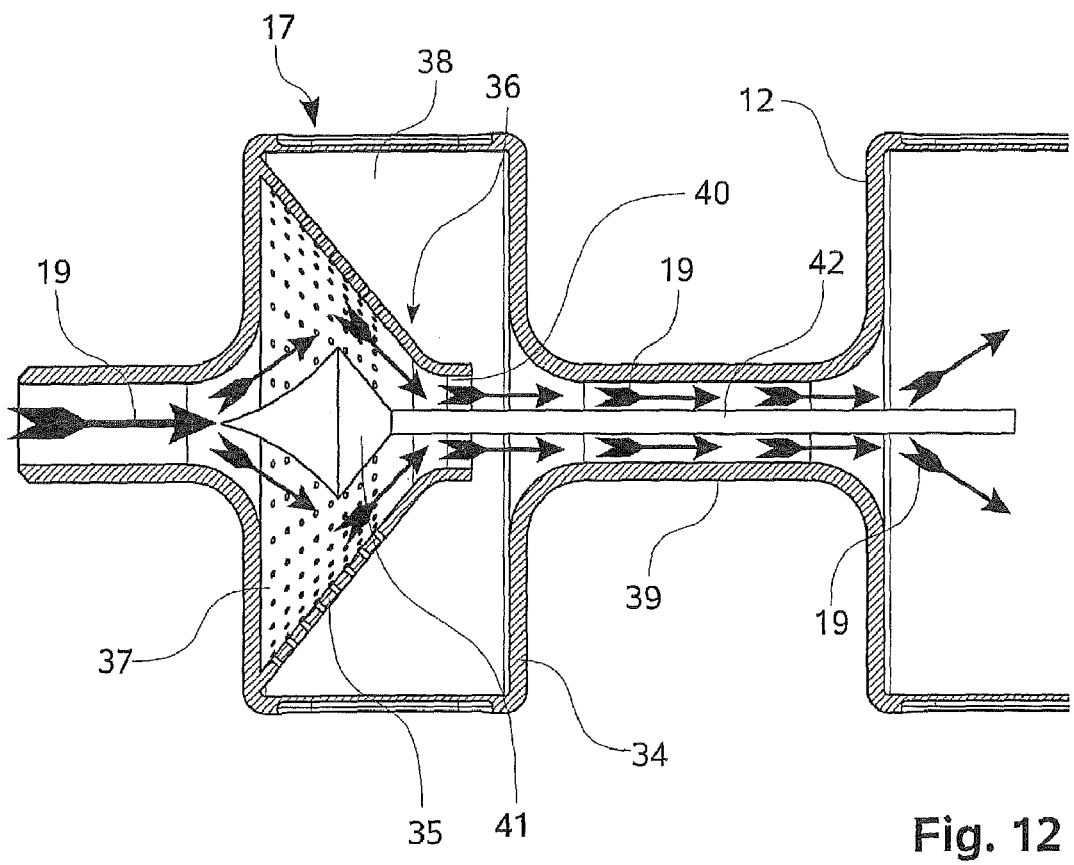
FIG. 12 shows the cross-sectional view of FIG. 10, the prefilter being in the emptying state.
Figure 13:
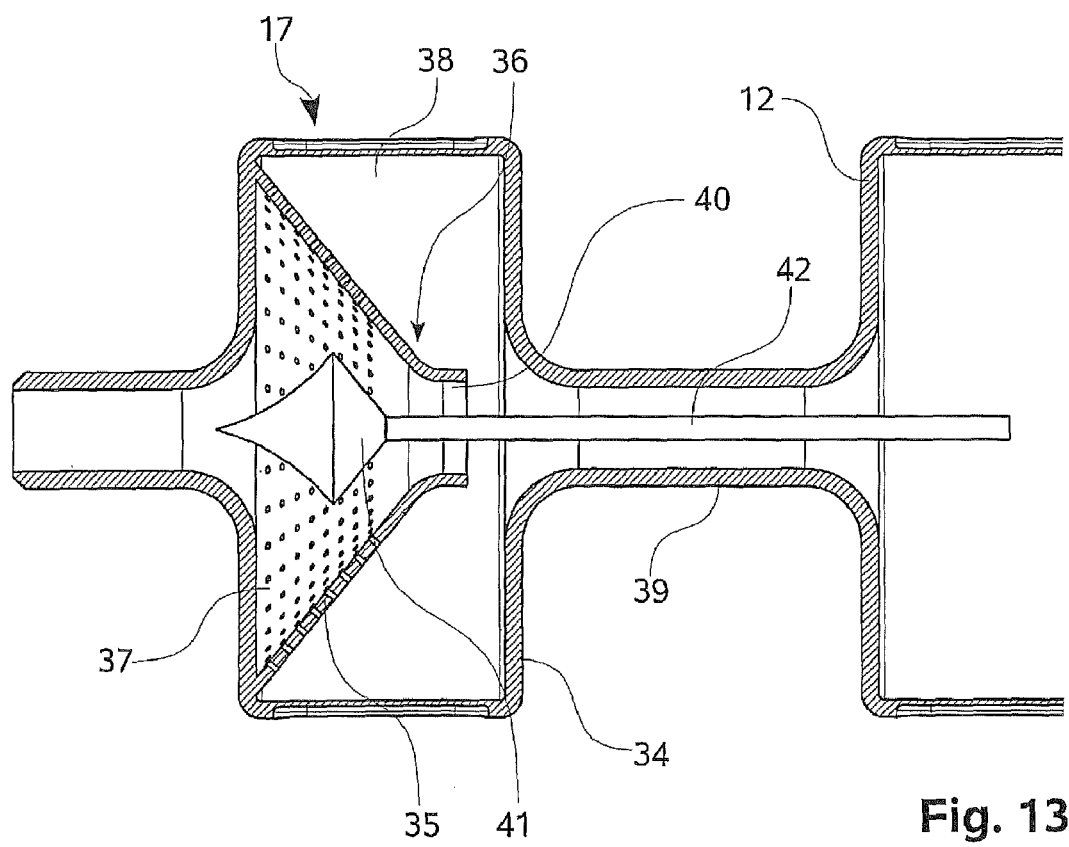
FIG. 13 shows the cross-sectional view of FIG. 12 without the added arrows identifying the air stream direction.

In FIGS. 12 and 13, valve 36 is shown in a second position in which closure piece 41 does not close off opening 40. With valve 36 in this position, air can accordingly pass directly through opening 40. In this context, histological sections or sectioning waste caught on filter region 35 are picked up by the air flow and conveyed through duct 39 to main filter 12. Prefilter 17 is accordingly in the emptying position with valve 36 in the state shown in FIGS. 12 and 13.

In conclusion, be it noted very particularly that the exemplifying embodiments discussed above serve merely to describe the teaching claimed, but do not limit it to the exemplifying embodiments.

List of Reference Numerals
1 Apparatus for isolating histological sections
2, 3 Histological section
4 Blade holder
5 Blade
6 Block
7 Cassette
8 Vertical motion direction of the block 6 and cassette 7
9 Horizontal motion direction of the blade holder 4
10 Nozzle device
11 Suction conduit
12 Main filter
13 Fan
14 Specimen slide
15 Constricted region of the suction conduit 11
16 Blade region
17 Prefilter
18 Filter cover
19 Direction of air stream flowing through the prefilter 17
20 Upstream duct
21 Filter insert
22 Downstream duct
23 Device for air reversal for the filter insert 21
24 One side of the filter insert 21
25 Second side of the filter insert 21
26 First connector part of the device for air reversal 23
27 Second connector part of the device for air reversal 23
28 Rotary member
29 Rotation axis of the rotary member
30 Housing part of the prefilter 17
31-33 Holes of the rotary member 28
34 Rectangular housing part of the prefilter 17
35 Filter region of the prefilter 17
36 Valve of the prefilter 17
37 First chamber of the prefilter 17
38 Second chamber of the prefilter 17
39 Duct between the prefilter 17 and the main filter 12
40 Opening
41 Closure piece of the valve 36 of the prefilter 17
42 Rod
FV Filter apparatus
T Depth of recess for the filter insert 21

What is claimed is:

1. An apparatus for filtering sectioning wastes of a microtome that are present in an air stream, having an aspiration device with which sectioning waste can be aspirated from a blade region of the microtome with an air stream, the aspiration device comprising:
    a main filter in which the sectioning wastes can be filtered from the air; and
    a prefilter for prefiltering the sectioning wastes, wherein the prefilter is arranged between the blade region and the main filter;
    the prefilter comprises a valve having two valve positions, wherein with the valve assuming a first valve position, the air stream flowing through the prefilter being directed into a flow direction provided for the filtering position; and with the valve in a second valve position that differs from the first valve position, the air stream flowing through the prefilter being directed into a flow direction provided for the emptying position; wherein
    the prefilter comprises a conical filter insert or a conical filter region that has at least one of a mesh-shaped, lattice-shaped, and hole-shaped structure that is configured substantially conically and tapers in the direction of the air stream;
    the valve is arranged at the downstream end of the conical filter insert or conical filter region of the prefilter;
    an opening is provided that can be closed off by the valve, wherein the valve closes the opening when assuming the first valve position so that the air stream is directed through the hole-shaped structure of the filter insert or filter region; and
    the valve opens the opening when assuming the second valve position so that almost the entire air stream is directed through the opening.

2. The apparatus according to claim 1, wherein the filtered contents of the prefilter is emptied to the main filter.

3. The apparatus according to claim 1, wherein the prefilter is designed so that sectioning wastes are retained by means of the prefilter; and so that the filtered sectioning wastes are conveyable to the main filter only when all the sections of a block that are to be produced with the microtome have been produced.

4. The apparatus according to claim 1, wherein the valve is actuated by one of manual and automatic action for emptying the prefilter.

5. The apparatus of claim 1, wherein the valve is actuated for emptying the prefilter by automatic action started by clamping a new block into the microtome.

6. The apparatus according to claim 1, comprising a means for temperature control cooling or heating at least one of the prefilter and the main filter.

7. The apparatus according to claim 1, wherein the main filter comprises a comminution unit by means of which the sectioning wastes in the main filter can be comminuted.

8. The apparatus according to claim 1, comprising an isolating device as described in the U.S. Patent Application published under the publication number US 2009/0181457, herewith incorporated by reference, by means of which the histological sections produced by the microtome can be isolated.

9. The apparatus according to claim 8, wherein said apparatus is at least one of allocated to or integrated in the nozzle device described in the U.S. Patent Application published under the publication number US 2009/0181457, herewith incorporated by reference.

10. A method for filtering sectioning wastes of a microtome that are present in an air stream by means of an apparatus having an aspiration device comprising a blade in a blade region, a main filter and a prefilter, said method comprising the method steps of:
    aspirating sectioning waste from the blade region of the microtome with an air stream;
    filtering sectioning wastes by means of the main filter from the air;
    arranging the prefilter between the blade region and the main filter;
    prefiltering the sectioning wastes from the air;
    emptying the filtered contents of the prefilter to the main filter; and shutting off the air stream immediately before emptying the prefilter.

11. The method according to claim 10, further comprising the method step of retaining the sectioning wastes on the prefilter as long as not all the sections of a block that are to be produced with the microtome have been produced; and conveying the filtered sectioning wastes to the main filter only after all the sections of a block that are to be produced with the microtome have been produced.

12. The method according to claim 10, further comprising the method step of conducting the emptying step of the prefilter in one of the two ways manually and automatically.

13. The method of claim 10, further comprising the method step of initiating the emptying step of the prefilter automatically when a new block is clamped into the microtome.

* * * * *